(12) United States Patent
Nakamura et al.

(10) Patent No.: US 9,508,916 B2
(45) Date of Patent: Nov. 29, 2016

(54) ULTRASONIC TRANSDUCER DEVICE, PROBE HEAD, ULTRASONIC PROBE, ELECTRONIC MACHINE AND ULTRASONIC DIAGNOSTIC APPARATUS

(71) Applicant: SEIKO EPSON CORPORATION, Tokyo (JP)

(72) Inventors: Tomoaki Nakamura, Nagano (JP); Yasunori Onishi, Nagano (JP); Kazuki Yoshida, Fujimi-machi (JP); Kogo Endo, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 268 days.

(21) Appl. No.: 14/051,563

(22) Filed: Oct. 11, 2013

(65) Prior Publication Data

US 2014/0103781 A1   Apr. 17, 2014

(30) Foreign Application Priority Data

Oct. 12, 2012  (JP) ................................. 2012-226671

(51) Int. Cl.
 *H01L 41/09* (2006.01)
 *B06B 1/06* (2006.01)
 *A61B 8/00* (2006.01)

(52) U.S. Cl.
 CPC ............. *H01L 41/09* (2013.01); *A61B 8/4483* (2013.01); *A61B 8/4494* (2013.01); *B06B 1/0622* (2013.01); *A61B 8/4405* (2013.01); *A61B 8/4411* (2013.01); *A61B 8/4427* (2013.01)

(58) Field of Classification Search
 CPC ........ H01L 41/09; B06B 1/06; B06B 1/0607
 USPC ......................................... 310/322, 334, 335
 See application file for complete search history.

(56) References Cited

U.S. PATENT DOCUMENTS

| | | | | |
|---|---|---|---|---|
| 7,288,069 | B2 * | 10/2007 | Takeuchi | B06B 1/0622 310/335 |
| 2003/0024317 | A1 | 2/2003 | Miller | |
| 2007/0251324 | A1 | 11/2007 | Wado et al. | |
| 2008/0116765 | A1 * | 5/2008 | Sugiura | B06B 1/0629 310/334 |
| 2013/0258802 | A1 | 10/2013 | Nakamura et al. | |
| 2013/0258803 | A1 | 10/2013 | Nakamura et al. | |

FOREIGN PATENT DOCUMENTS

| | | |
|---|---|---|
| JP | 2005-354582 A | 12/2005 |
| JP | 2009-055644 A | 3/2009 |
| JP | 2011-082624 A | 4/2011 |
| WO | 2011/094393 A1 | 8/2011 |

OTHER PUBLICATIONS

The Extended European Search Report for the corresponding European Application No. 13188051.0 dated Oct. 21, 2015.

* cited by examiner

*Primary Examiner* — Derek Rosenau
(74) *Attorney, Agent, or Firm* — Global IP Counselors, LLP

(57) ABSTRACT

An ultrasonic transducer device includes a substrate on which a plurality of openings are arranged; a plurality of ultrasonic transducer elements, each of the ultrasonic transducer elements being provided to each of the openings of the plurality of openings, on a first surface of the substrate; and a member fixed to a second surface of the substrate, which is a surface on the opposite side of the first surface of the substrate. Provided to the member are a plurality of first groove sections, and a second groove section for bundling together the plurality of the first groove sections.

14 Claims, 10 Drawing Sheets

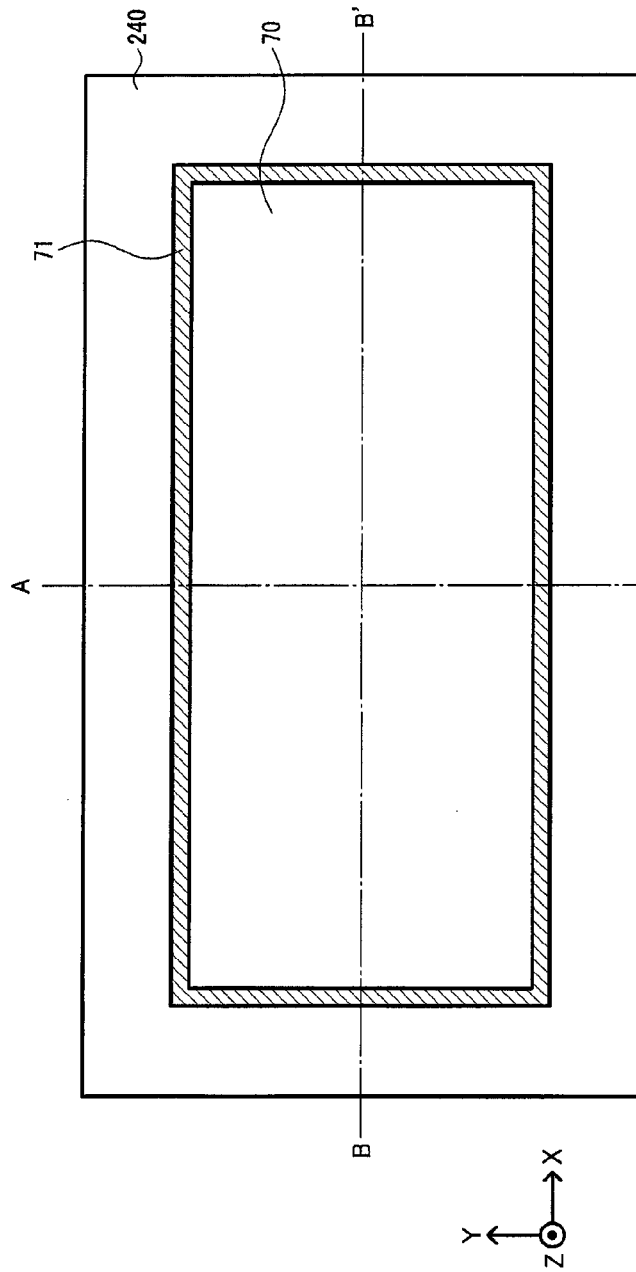
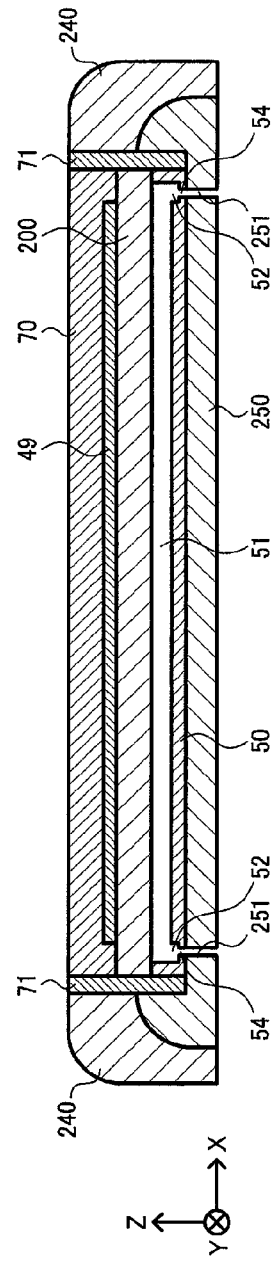
Fig. 3A
Fig. 3B

ULTRASONIC TRANSDUCER DEVICE, PROBE HEAD, ULTRASONIC PROBE, ELECTRONIC MACHINE AND ULTRASONIC DIAGNOSTIC APPARATUS

CROSS-REFERENCE TO RELATED APPLICATIONS

This application claims priority to Japanese Patent Application No. 2012-226671 filed on Oct. 12, 2012. The entire disclosure of Japanese Patent Application No. 2012-226671 is hereby incorporated herein by reference.

BACKGROUND

1. Technical Field

The present invention relates to an ultrasonic transducer device, a probe head, an ultrasonic probe, an electronic machine, an ultrasonic diagnostic apparatus, and the like.

2. Related Art

One known example of an apparatus for insonifying a subject with ultrasonic waves and receiving reflected waves coming from an interfacial surface at which the acoustic impedance is different within the interior of the subject is an ultrasonic diagnostic apparatus for inspecting the interior of a human body. For example, Japanese Laid-open Patent Publication 2011-82624 discloses a technique in which a transducer element comprising a piezoelectric body layer and an electrode layer is formed on a substrate, as an ultrasonic transducer device to be used in an ultrasonic diagnostic apparatus.

However, in this technique, a plurality of openings are provided to the substrate, and therefore the strength of the substrate has been diminished, and the ultrasonic transducer device has been damaged by pressure from the exterior, among other problems.

SUMMARY

According to several aspects of the present invention, it is possible to provide an ultrasonic transducer device, a probe head, an ultrasonic probe, an electronic machine, an ultrasonic diagnostic apparatus, and the like by which the strength is raised and any decline in element properties can be minimized.

According to one aspect of the invention, an ultrasonic transducer device includes: a substrate on which a plurality of openings are arranged; a plurality of ultrasonic transducer elements, each of the ultrasonic transducer elements being provided to each of the openings of the plurality of openings, on a first surface of the substrate; and a reinforcement member for reinforcing the substrate, the reinforcement member being fixed to a second surface of the substrate, which is a surface on the opposite side of the first surface of the substrate, a plurality of first groove sections formed so as to oppose the plurality of openings of the substrate and second groove sections for bundling together the plurality of first groove sections being provided to the reinforcement member.

According to the one aspect of the invention, the reinforcement member is fixed to the second surface of the substrate, and thus the strength of the ultrasonic transducer elements and of the substrate can be increased. Also, the plurality of openings can be in communication with each other via the first groove sections, and the bundling together of the plurality of first groove sections by the second groove sections also makes it possible for the plurality of first groove sections to be in communication with each other.

According to another aspect of the invention, the reinforcement member may include through holes perforating in the thickness direction of the reinforcement member, by which communication is provided between the second groove sections and an external space, and the plurality of first groove sections, the second groove sections, and the through holes may form ventilation channels by which communication is provided between the openings of the substrate and the external space.

In so doing, the openings are not sealed off but rather ventilation with the external space can be ensured, and thus it becomes possible to avoid problems such as, for example, any decline in element properties caused by sound pressure being locked in during actual operation, or element damage caused by the air inside the openings swelling and contracting due to temperature changes.

According to another aspect of the invention, third groove sections which are in communication with the external space but are not in communication with the plurality of first groove sections nor the second groove sections may be provided to a region opposite the surrounding region of the opening region of the substrate, on a surface of the reinforcement member that is bonded to the substrate.

In so doing, providing the third groove sections makes it possible for air between the reinforcement member and the substrate to escape to the external space when the reinforcement member is being adhered to the substrate, and therefore makes it possible to improve the adhesion between the reinforcement member and the substrate.

According to another aspect of the invention, the plurality of first groove sections may be provided along a first direction to a region opposing an opening region of the substrate on the surface of the reinforcement member that is bonded to the substrate, the second groove sections may be provided along a second direction intersecting with the first direction to a region opposing a surrounding region of the opening region of the substrate on the surface of the reinforcement member that is bonded to the substrate, and at least one end of each of the first groove sections of the plurality of first groove sections may be joined to the second groove sections in a region opposing the surrounding region of the opening region of the substrate.

In so doing, the plurality of first groove sections can be provided to the region opposing the opening region of the substrate on the surface of the reinforcement member that is bonded to the substrate, and the second groove sections can be provided to the region surrounding the region to which the plurality of first groove sections are provided. One end of each of the first groove sections of the plurality of first groove sections can then be joined to the second groove sections. So doing makes it possible for the second groove sections to bundle together the plurality of first groove sections.

According to another aspect of the invention, third groove sections that are in communication with the external space but are not in communication with the plurality of first groove sections nor with the second groove sections may be provided to a region opposing the surrounding region of the opening region of the substrate on the surface of the reinforcement member that is bonded to the substrate, the third groove sections either being provided along the first direction on regions that run along edges of the reinforcement member on the first direction side or edges on the opposite side to the first direction, or being provided along the second direction on regions that run along edges of the reinforcement member on the second direction side or edges on the opposite side to the second direction, and one end of the third groove sections being separated from both the plurality of first groove sections and the second groove sections and the other end of the third groove sections being bonded to the edges of the reinforcement member.

In so doing, the third groove sections can be arranged along the four edges of the reinforcement member, and thus the adhesion between the reinforcement member and the substrate can be enhanced.

According to another aspect of the invention, the reinforcement member may be bonded in at least one bonding region to partition wall sections for separating each of the openings of the plurality of openings arranged in an arrayed shape.

In so doing, constraining the movement of the partition wall sections by the reinforcement member makes it possible to minimize vibration of the partition wall sections. As a result, for example, cross-talk between adjacent ultrasonic transducer elements can be reduced.

According to another aspect of the invention, each of the ultrasonic transducer elements of the plurality of ultrasonic transducer elements may include a vibrating membrane for covering the opening and a piezoelectric element section provided on the vibrating membrane, the piezoelectric element section including a lower electrode provided on the vibrating membrane, a piezoelectric body membrane provided so as to at least partially cover the lower electrode, and an upper electrode provided so as to at least partially cover the piezoelectric body membrane.

In so doing, changing the voltage difference between the voltage of the upper electrode and the voltage of the lower electrode causes the piezoelectric body membrane to expand and contract, and causes the vibrating membrane to vibrate, whereby the ultrasonic transducer elements can emit ultrasonic waves.

According to another aspect of the invention, a probe head includes any of the ultrasonic transducer devices described above.

According to another aspect of the invention, an ultrasonic probe includes the probe head described above, and a processing apparatus for processing a signal coming from the ultrasonic transducer device.

According to another aspect of the invention, an electronic machine includes any of the ultrasonic probes described above.

According to another aspect of the invention, an ultrasonic diagnostic apparatus includes any of the ultrasonic probes described above and a display unit configured to display display image data.

BRIEF DESCRIPTION OF THE DRAWINGS

Referring now to the attached drawings which form a part of this original disclosure:

FIG. 3A is an example of mounting for an ultrasonic transducer device;

FIG. 3B is the example of mounting for the ultrasonic transducer device;

DETAILED DESCRIPTION OF EXEMPLARY EMBODIMENTS

The following describes in greater detail a preferred embodiment of the present invention. The present embodiment described below is not, however, meant to gratuitously limit the content of the present invention described in the claims, nor is the entire configuration described in the present embodiment necessarily essential in terms of the solution of the present invention.

1. Ultrasonic Transducer Element

Figure 1A:
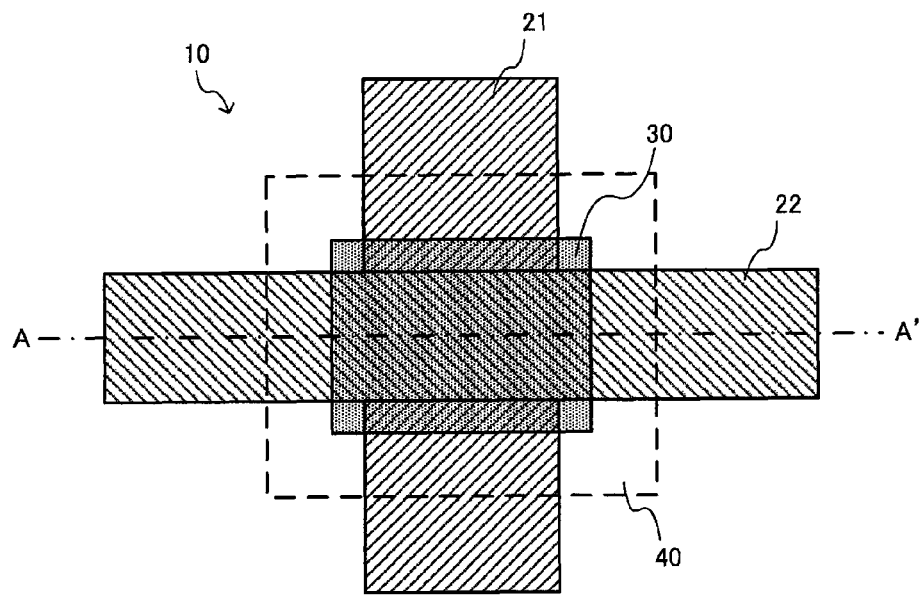
FIG. 1A is an example of a basic configuration for an ultrasonic transducer element.
Figure 1B:
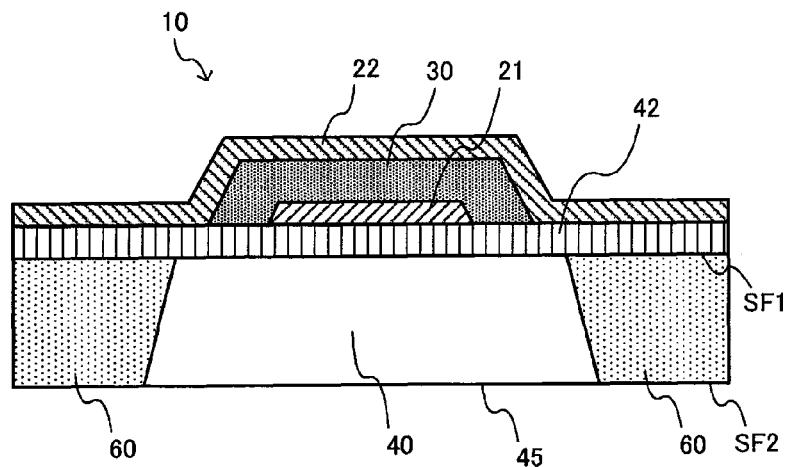
FIG. 1B are the example of the basic configuration for the ultrasonic transducer element.

FIGS. 1A and 1B illustrate an example of a basic configuration for an ultrasonic transducer element (a thin-film piezoelectric ultrasonic transducer element) 10 included in an ultrasonic transducer device of the present embodiment. The ultrasonic transducer element 10 of the present embodiment includes a vibrating membrane (membrane, support membrane) 42 and a piezoelectric element section. The piezoelectric element section includes a lower electrode (first electrode layer) 21, a piezoelectric body membrane (piezoelectric body layer) 30, and an upper electrode (second electrode layer) 22. The ultrasonic transducer element 10 of the present embodiment is not limited to being the configuration of FIGS. 1A and 1B, but rather a variety of modifications can be implemented, such as omitting a part of the constituent elements thereof, replacing same with other constituent elements, or adding other constituent elements.

In the following description, the ultrasonic transducer element is also called an "ultrasonic element 10".

FIG. 1A is a plan view of the ultrasonic element 10, which is formed on a substrate (silicon substrate) 60, as seen from a direction perpendicular to the substrate on an element formation surface side. FIG. 1B is a cross-sectional view illustrating a cross-section taken along the A-A' line in FIG. 1A. In the substrate 60, a surface on the side where the element is formed is understood to be a first surface SF1, and the surface on the opposite side of the first surface SF1 is understood to be a second surface SF2.

The first layer 21 is formed of, for example, a metal thin film, on an upper layer of the vibrating membrane 42. The first electrode layer 21 may be a wiring that extends to the outside of an element formation region, as illustrated in FIG. 1A, and is connected to an adjacent ultrasonic element 10.

The piezoelectric body membrane 30 is formed of, for example, a lead zirconate titanate (PZT) thin film, and is provided so as to at least partially cover the first electrode layer 21. The material of the piezoelectric body membrane 30, however, is not limited to being PZT, but rather, for example, lead titanate (PbTiO3), lead zirconate (PbZrO3), lanthanum lead titanate ((Pb, La)TiO3), or the like may be used.

The second electrode layer 22 is formed of, for example, a metal thin film, and is provided so as to at least partially cover the piezoelectric body membrane 30. The second electrode layer 22 may be a wiring that extends to the outside of the element formation region, as illustrated in FIG. 1A, and is connected to an adjacent ultrasonic element 10.

The vibrating membrane (membrane) 42 is provided so that an opening 45 is covered by, for example, a two-layered structure of an SiO2 thin film and a ZrO2 thin film. The vibrating membrane 42 supports the piezoelectric body membrane 30 and the first and second electrode layers 21, 22, and is able to vibrate in conformity with the expansion and contraction of the piezoelectric body membrane 30 to generate ultrasonic waves.

The opening 45 is arranged on the substrate 60. A cavity region 40 created by the opening 45 is formed by etching by reactive ion etching (RIE) or the like from a reverse surface of the substrate 60 (the surface on which the element is not formed).

The lower electrode of the ultrasonic element 10 is formed of the first electrode layer 21 and the upper electrode is formed of the second electrode layer 22. More specifically, the portion of the first electrode layer 21 that is covered by the piezoelectric body membrane 30 forms the lower electrode, and the portion of the second electrode layer 22 that covers the piezoelectric body membrane 30 forms the upper electrode. That is to say, the piezoelectric body membrane 30 is provided sandwiched between the lower electrode and the upper electrode.

The piezoelectric body membrane 30 is expanded and contracted in an in-plane direction by the application of a voltage between the lower electrode and the upper electrode, i.e., between the first electrode layer 21 and the second electrode layer 22. The ultrasonic element 10 uses a monomorph (unimorph) structure obtained by bonding together a thin piezoelectric element section and the vibrating membrane 42, and when the piezoelectric element section undergoes in-plane expansion and contraction, warping takes place because the dimensions of the vibrating membrane 42 remain unaffected. As such, applying an alternating current voltage to the piezoelectric body membrane 30 causes the vibrating membrane 42 to vibrate with respect to the film thickness direction, and the vibration of the vibrating membrane 42 causes ultrasonic waves to be emitted. The voltage that is applied to the piezoelectric body membrane 30 is, for example, 10 to 30 V, and the frequency is, for example, 1 to 10 MHz.

In contrast to the fact that the drive voltage for bulk ultrasonic elements would be about 100 V in peak-to-peak, the drive voltage could be reduced to about 10 to 30 V in peak-to-peak in a thin-film piezoelectric ultrasonic element 10 as is illustrated in FIGS. 1A and 1B.

The ultrasonic element 10 also operates as a receiver element for receiving an ultrasonic echo produced when emitted ultrasonic waves are reflected by a subject and then come back. The ultrasonic echo causes the vibrating membrane 42 to vibrate, and this vibration causes a pressure to be applied to the piezoelectric body membrane 30 and causes a voltage to be generated between the lower electrode and the upper electrode. This voltage can be extracted as a received signal.

2. Ultrasonic Transducer Device

Figure 2:
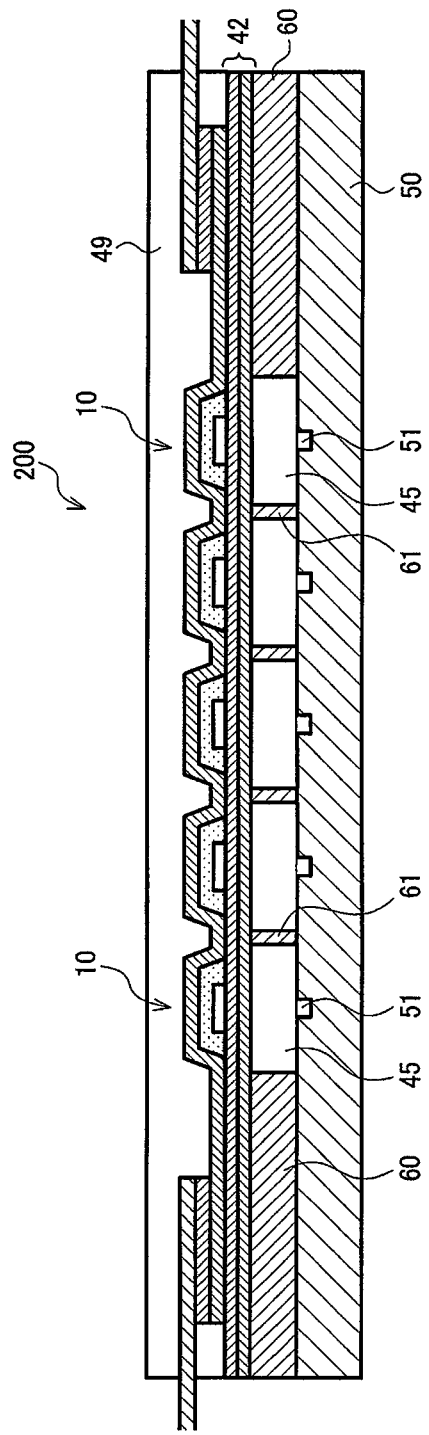
FIG. 2 is a cross-sectional view of an example of a configuration for an ultrasonic transducer device.

FIG. 2 is a cross-sectional view of an example of an example for an ultrasonic transducer device 200 of the present embodiment. The ultrasonic transducer device 200 includes a plurality of the ultrasonic transducer element 10, the substrate 60, and a reinforcement member 50. The ultrasonic transducer device 200 of the present embodiment is not limited to being the configuration of FIG. 2, but rather a variety of modifications can be implemented, such as omitting a part of the constituent elements thereof, replacing same with other constituent elements, or adding other constituent elements.

For the ultrasonic transducer elements 10, the element illustrated in FIGS. 1A and 1B can be used.

The substrate 60 is, for example, a silicon substrate, and includes a plurality of the opening 45, which are arranged in an arrayed shape. On the first surface SF1 of the substrate 60, the ultrasonic transducer elements 10 are provided so as to correspond to each of the plurality of openings 45.

The reinforcement member 50 is fixed to the second surface SF2 of the substrate 60, which is the surface on the opposite side of the first surface SF1 of the substrate 60, and reinforces the substrate 60. The reinforcement member 50 is formed, for example, by etching a silicon substrate. Alternatively, the reinforcement member 50 is formed by microprocessing a metal sheet. A plurality of first groove sections 51 are provided to a surface of the reinforcement member 50 that is bonded to the substrate 60 (see FIG. 5). The first groove sections 51 are, for example, rectilinear grooves. That is to say, the plurality of openings 45, which oppose the first groove sections 51, are in communication with each other via the first groove sections 51. The cross-sectional shape of the first groove sections 51 may be quadrangular, triangular, semicircular, or another shape.

The reinforcement member 50 is bonded, in at least one bonding region, to partition wall sections 61 separating each of the plurality of openings 45 arranged in an arrayed shape. The partition wall sections 61 are provided between adjacent openings 45, and adjacent openings 45 are partitioned from each other by the partition wall sections 61. The bonding could involve the use of an adhesive. In so doing, movement of the partition wall sections 61 would be constrained by the reinforcement member 50, and thus any vibration of the partition wall sections 61 can be minimized. As a result, cross-talk between the ultrasonic transducer elements 10 can be reduced.

Figure 5:
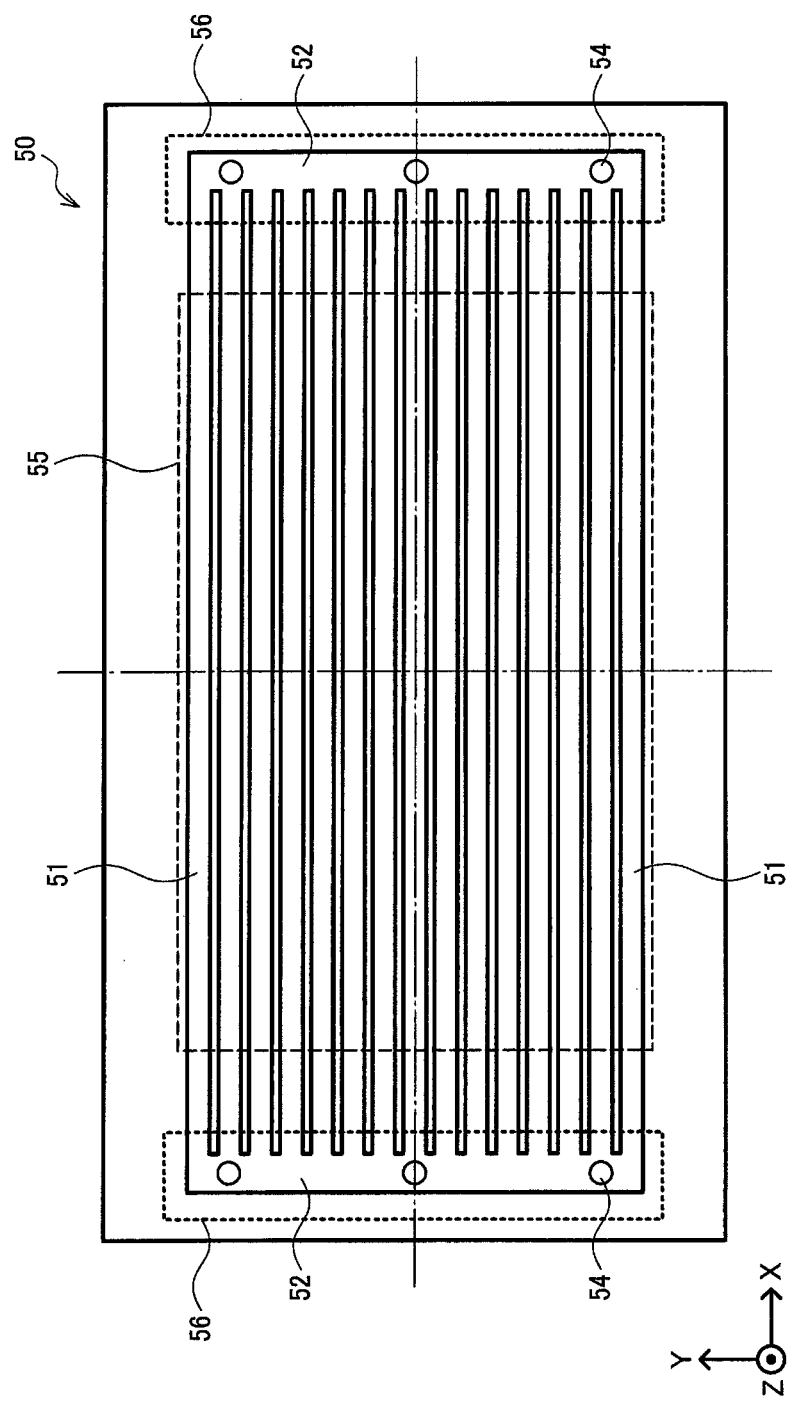
FIG. 5 is an example of a first configuration for a reinforcement member.

Further provided to the surface of the reinforcement member 50 that is bonded to the substrate 60 are second groove sections 52, as illustrated in FIGS. 3B and 5, to be described below. The second groove sections 52 bundle together the plurality of first groove sections 51.

A protective film 49 is layered onto the surface of the ultrasonic transducer device 200. The protective film 49 is coated to cover, for example, the full surface of the ultrasonic transducer device 200. The protective film 49 protects the plurality of ultrasonic transducer elements 10 arranged in an arrayed shape, and also functions as an acoustic matching layer. For the protective film 49, it would be possible to use, for example, a silicone resin film.

Figure 4:
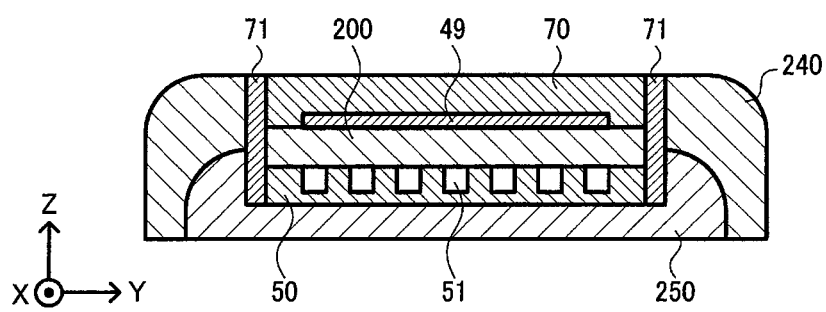
FIG. 4 is an example of mounting for an ultrasonic transducer device.

FIGS. 3A, 3B, and 4 illustrate an example of mounting of the ultrasonic transducer device 200 onto an ultrasonic probe (probe head). FIG. 3A is a plan view; FIG. 3B is a cross-sectional view taken along the B-B' line; and FIG. 4 is a cross-sectional view taken along the A-A' line. FIGS. 3B and 4 do not depict the details of the structure of the ultrasonic transducer device 200. The mounting of the ultrasonic transducer device 200 is not limited to what is illustrated in FIGS. 3A, 3B, and 4, but rather a variety of methods would be feasible.

The protective film is layered onto the surface of the ultrasonic transducer device 200, and further formed thereon is an acoustic lens 70. The reverse surface of the ultrasonic transducer device 200 is fixed to a probe base 250. A side surface of the ultrasonic transducer device 200 is enclosed by a probe housing 240 and by the probe base 250, with a protective layer 71 interposed therebetween. That is to say, the ultrasonic transducer device 200 is supported by the probe housing 240 and the probe base 250. The protective layer 71 can be formed of, for example, the same silicone resin as that of the protective film 49.

Provided to the reinforcement member 50 of the ultrasonic transducer device 200 are the pluralities of first groove sections 51 and second groove sections 52, and through holes 54. The first groove sections 51 oppose the plurality of openings 45, and the second groove sections 52 bundle together the plurality of first groove sections 51. The through holes 54 provide communication between the second groove sections 52 and the external space. As a result, the first groove sections 51, the second groove sections 52, and the through holes 54 form ventilation channels that provide communication between the openings 45 of the substrate 60 and the external space.

More specifically, as illustrated in FIG. 3B, the plurality of first groove sections 51 are provided along the X-direction. The second groove sections 52 are provided along the Y-direction, on a short edge side of the reinforcement member 50. The plurality of openings 45, which are arranged, for example, along the B-B' line, are in communication with each other via the first groove sections 51 that are provided along the B-B' line. One end of the first groove sections 51 is joined to one second groove section 52 and the other end of the first groove sections 51 is joined to another second groove section 52. Communication is provided between the second groove sections 52 and the external space via the through holes 54, and also the through holes 54 are joined to through holes 251 provided to the probe base 250. As a result, the plurality of openings arranged along the B-B' line are in communication with the external space.

In this manner, according to the ultrasonic transducer device 200 of the present embodiment, ventilation channels that provide communication between each of the openings 45 and the external space can be formed. So doing causes the internal space of the openings 45 to not be sealed off and thus makes it possible to ensure ventilation with the external space. Were the internal space of the openings 45 to be hermetically sealed, problems would arise such as in that sound pressure would be locked in during actual operation, diminishing the transmission and reception properties, or in that temperature changes would cause the air in the internal space to swell or contract, thus changing the element properties. Depending on the case, the vibrating membrane 42 could be damaged. In the ultrasonic transducer device 200 of the present embodiment, the internal space of the openings 45 is readily able to follow pressure fluctuations in the surroundings, and thus the ultrasonic transducer element 10 is able to avoid the problems described above. Herein, the external space signifies a space that is separated from the internal space by, for example, the substrate 60, the vibrating membrane 42, and the reinforcement member 50, and that is significantly larger than the internal space.

FIG. 5 illustrates a first configuration example of the reinforcement member 50. The reinforcement member 50 of the first configuration example includes the pluralities of first groove sections 51, second groove sections 52, and through holes 54. The X-, Y-, and Z-directions illustrated in FIG. 5 correspond to the X-, Y-, and Z-directions illustrated in FIGS. 3A, 3B, and 4. The reinforcement member 50 of the present embodiment is not limited to being the configuration of FIG. 5, but rather a variety of modifications can be implemented, such as omitting a part of the constituent elements thereof, replacing same with other constituent elements, or adding other constituent elements.

The plurality of first groove sections 51 are provided along the X-direction (more broadly, a first direction) to a region 55 opposing an opening region of the substrate 60, on the surface of the reinforcement member 50 that is bonded to the substrate 60. The opening region refers to a region where the openings 45 are arranged in an arrayed shape on the substrate 60. The region 55 opposing the opening region refers to a region that opposes the opening region on the reinforcement member 50 in a case where the reinforcement member 50 has been fixed to the substrate 60. So doing allows the first groove sections 51 to form the ventilation channels communicating through the plurality of openings 45 in a case where the reinforcement member 50 has been fixed to the substrate 60.

The second groove sections 52 are provided along the Y-direction (more broadly, a second direction intersecting with the first direction) to a region 56 opposing a surrounding region of the opening region of the substrate 60, on the surface of the reinforcement member 50 that is bonded to the substrate 60. The surrounding region of the opening region refers to a region surrounding the region where the openings 45 are arranged in an arrayed shape on the substrate 60. The region 56 opposing the surrounding region of the opening region refers to a region that opposes the surrounding region of the opening region on the reinforcement member 50 in a case where the reinforcement member 50 has been fixed to the substrate 60. That is to say, the region 56 opposing the surrounding region of the opening region does not oppose the region in which the plurality of openings 45 are arranged in an arrayed shape on the substrate 60 in a case where the reinforcement member 50 has been fixed to the substrate 60.

One end of each of the first groove sections of the plurality of first groove sections 51 is joined to the second groove sections 52 in the region 56 opposing the surrounding region of the opening region of the substrate 60. That is to say, the second groove sections 52 bundle together the plurality of first groove sections 51.

The through holes 54 provide communication between the second groove sections 52 and the external space. So doing allows for the first groove sections 51, the second groove sections 52, and the through holes 54 to form the ventilation channels providing communication between the openings 45 of the substrate 60 and the external space.

For example, as illustrated in FIG. 5, the first groove sections 51 are provided along the X-direction in the region 55 opposing the opening region. The second groove sections 52 are provided along the Y-direction in the region 56 on the short edge side of the reinforcement member 50 (more broadly, in the region opposing the surrounding region of the opening region). One of two second groove sections 52 is joined to one end of the first groove sections 51, and the other of two second groove sections 52 is joined to the other end of the first groove sections 51. The through holes 54 are perforated through the second groove sections 52 and a reverse surface (a surface not bonded to the substrate 60) of the reinforcement member 50. There can be a plurality of the through holes 54 provided.

The first groove sections 51 may also be provided along the Y-direction in the region 55 opposing the opening region. In such a case, the second groove sections 52 would be provided along the X-direction in a region on a long edge side of the reinforcement member 50.

Figure 6:
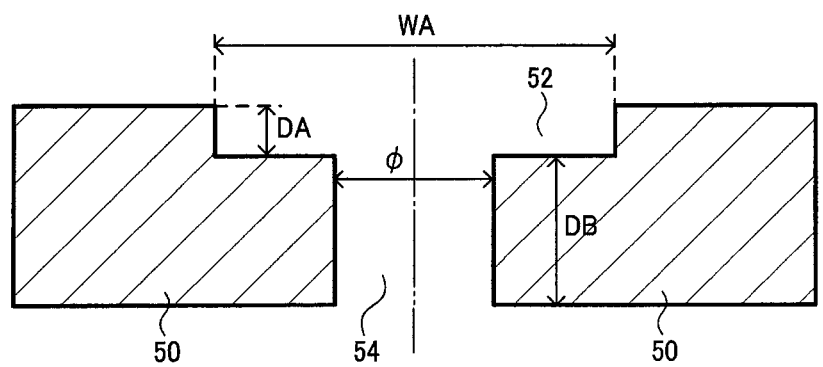
FIG. 6 is a cross-sectional view of a through hole.

FIG. 6 is a cross-sectional view of the through holes 54 of the first configuration example of the reinforcement member 50. A width WA of the second groove sections 52 is greater than a diameter φ of the through holes 54. For example, WA=1 mm, φ=0.4 mm. The depth DA of the second groove sections 52 is, for example, 0.1 mm, and the depth DB of the through holes 54 is, for example, 0.4 mm.

Figure 7:
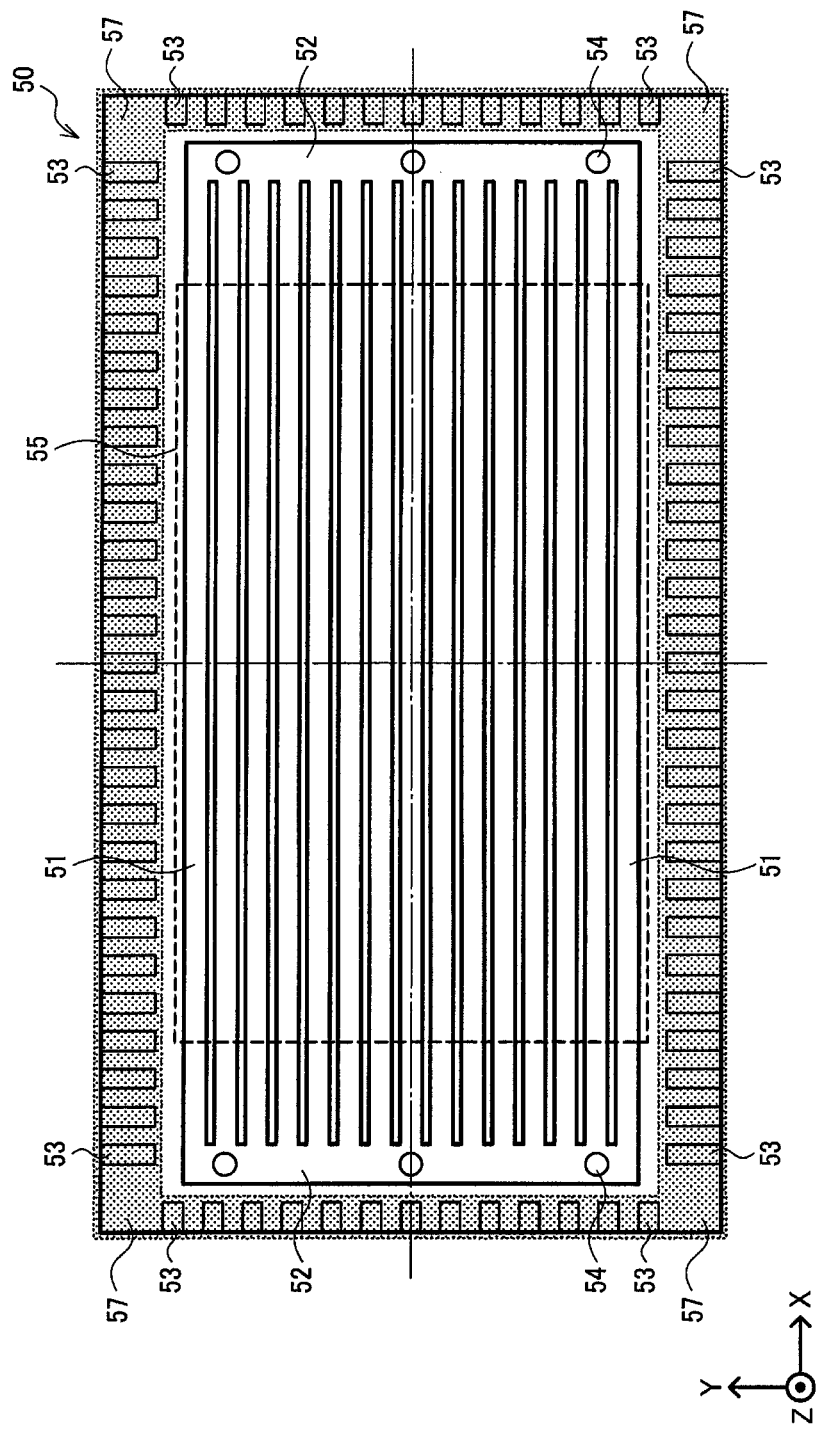
FIG. 7 is an example of second configuration for a reinforcement member.

FIG. 7 illustrates a second configuration example of the reinforcement member 50. The reinforcement member 50 of the second configuration example includes the first groove sections 51, the second groove sections 52, third groove sections 53, and the through holes 54. The X-, Y-, and Z-directions illustrated in FIG. 7 correspond to the X-, Y-, and Z-directions illustrated in FIGS. 3A, 3B, and 4. The first groove sections 51, the second groove sections 52, and the through holes 54 are the same as those of the first configuration example described above (see FIG. 5), and thus a more detailed description thereof has been omitted.

The third groove sections 53 are provided to a region 57 opposing the surrounding region of the opening region of the substrate 60, on the surface of the reinforcement member 50 that is bonded to the substrate 60, and are in communication with the external space but are not in communication with any of the first groove sections 51 or second groove sections 52. The region 57 opposing the surrounding region of the opening region refers to a region opposing the surrounding region of the opening region on the reinforcement member 50 in a case where the reinforcement member 50 has been fixed to the substrate 60. The third groove sections 53 may also be provided to a region 57 opposing the surrounding region of the opening region running along the four edges of the reinforcement member 50.

The third groove sections 53 are provided along the X-direction, in a region that runs along either the edges of the reinforcement member 50 on the X-direction (more broadly, first direction) side or along the edges on the opposite side to the X-direction. Alternatively, the third groove sections 53 are provided along the Y-direction, in a region that runs along the edges of the reinforcement member 50 on the Y-direction (more broadly, the second direction) side or along the edges on the opposite side to the Y-direction. One end of the third groove sections 53 is separated from both the pluralities of first groove sections 51 and second groove sections 52, and the other end of the third groove sections 53 is bonded to the edge of the reinforcement member 50.

More specifically, as illustrated in, for example, FIG. 7, the plurality of third groove sections 53 are provided in the region 57 opposing the surrounding region of the opening region running along the four edges of the reinforcement member 50. The one end of the third groove sections 53 is not joined to either the first groove sections 51 or second groove sections 52. The other end of the third groove sections 53, however, is bonded to the edge (end surface) of the reinforcement member 50. The third groove sections 53 are provided to the region 57 (more broadly, the region opposing the surrounding region of the opening region) on the outside of the regions to which the pluralities of first groove sections 51 and second groove sections 52 are provided.

Providing the third groove sections 53 makes it possible for air between the reinforcement member 50 and the substrate 60 to escape to the external space when the reinforcement member 50 is being adhered to the substrate 60, and therefore makes it possible to improve the adhesion between the reinforcement member 50 and the substrate 60.

Figure 8A:
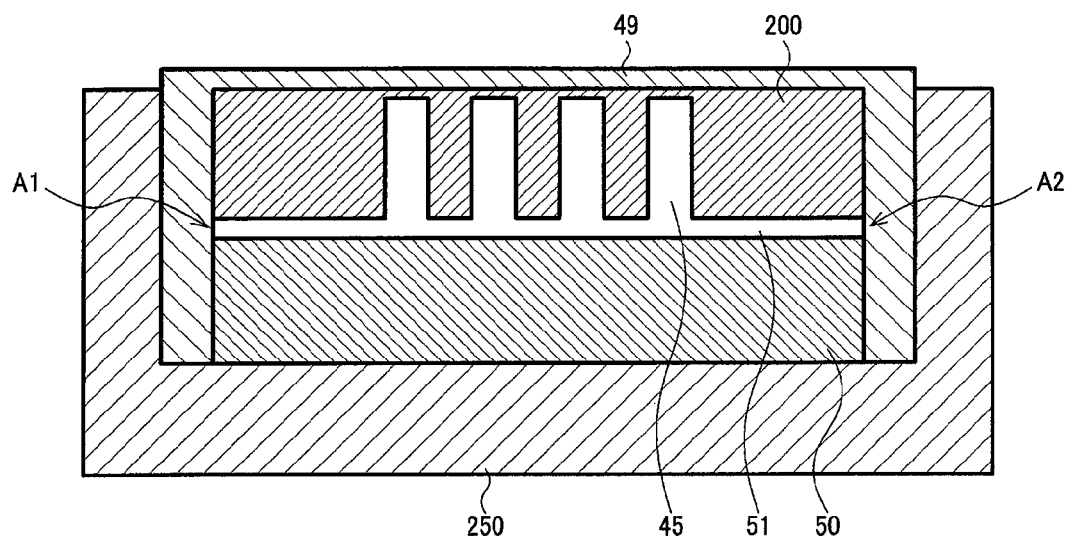
FIG. 8A is a drawing for describing a reason why it would be desirable for through holes to be provided to a reverse surface of a reinforcement member.
Figure 8B:
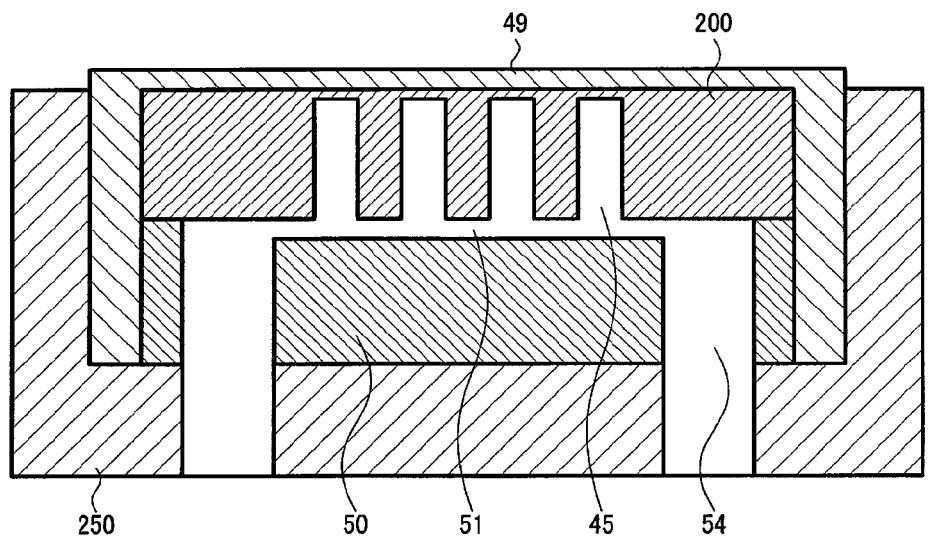
FIG. 8B is the drawing for describing the reason why it would be desirable for the through holes to be provided to the reverse surface of the reinforcement member.

FIGS. 8A and 8B are drawings for describing a reason why it would be desirable for the through holes 54 to be provided to a reverse surface of the reinforcement member 50. FIG. 8A illustrates a case where the through holes 54 are provided to a side surface, by way of comparative example, and FIG. 8B illustrates a case where the through holes 54 are provided to the reverse surface.

The ultrasonic transducer device 200 is placed onto a recess of the probe base 250, and a resin for forming the protective film 49 is poured in from above. At this time, in the case where the through holes 54 are provided to the side surface, the through holes 54 become plugged up with the resin, as illustrated by A1 and A2 of FIG. 8A. In the case where the through holes 54 are provided to the reverse surface, however, the through holes 54 are not plugged up with the resin.

This manner of providing the through holes 54 to the reverse surface of the reinforcement member 50 prevents the through holes 54 from being plugged up with the resin when the resin for forming the protective film 49 is being poured in, and thus makes it possible to ensure the ventilation channels providing communication between each of the openings 45 and the external space.

The method of mounting the ultrasonic transducer device 200 is not limited to being what is illustrated in FIGS. 8A and 8B, but rather may be another method of mounting. Also, in a case where there is no concern that the through holes 54 might be plugged up with the resin, then the through holes 54 may be provided to a location other than the reverse surface of the reinforcement member 50, e.g., the side surface.

As described above, according to the ultrasonic transducer device 200 of the present embodiment, the reinforcement member 50 is fixed to the substrate 60, and thus the strength of the ultrasonic transducer element 10 and of the substrate 60 can be increased. Also, because the openings 45 provided to the substrate 60 are not sealed off but rather ventilation with the external space can be ensured, it becomes possible to avoid problems such as, for example, any decline in element properties caused by sound pressure being locked in during actual operation, or element damage caused by the air inside the openings swelling and contracting due to temperature changes. Further, the reinforcement member 50 can minimize any vibration of the partition wall sections 61, and thus it is possible, for example, to reduce cross-talk between adjacent ultrasonic transducer elements 10. As a result, it becomes possible to implement an ultrasonic transducer device that has high strength and is able to minimize any decline in element properties.

Figure 9:
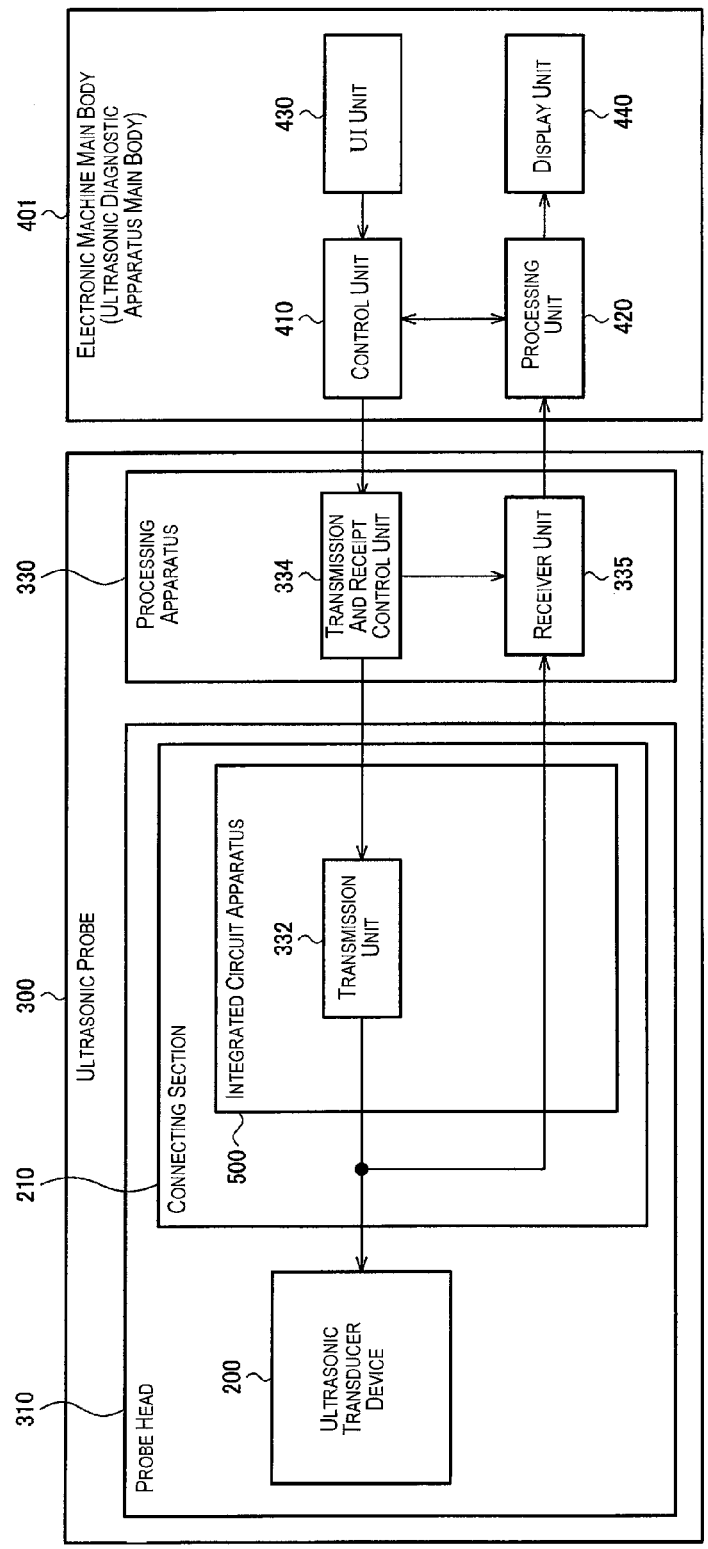
FIG. 9 is an example of a basic configuration for an electronic machine (an ultrasonic diagnostic apparatus)

3. Ultrasonic Probe, Probe Head, Electronic Machine, and Ultrasonic Diagnostic Apparatus FIG. 9 illustrates an example of a basic configuration for an electronic machine (ultrasonic diagnostic apparatus) of the present embodiment. The ultrasonic diagnostic apparatus includes an ultrasonic probe 300 and an ultrasonic diagnostic apparatus main body 401. The ultrasonic probe 300 has a probe head 310 and a processing apparatus 330. The ultrasonic diagnostic apparatus main body 401 has a control unit 410, a processing unit 420, a user interface unit (UI unit) 430, and a display unit 440.

The processing apparatus 330 includes a transmission and reception control unit 334 and a receiver unit 335 (an analog front-end unit). The probe head 310 includes the ultrasonic transducer device 200, as well as a connecting section 210 (connector section) for connecting the ultrasonic transducer device 200 to a circuit board (for example, a rigid substrate). Implemented on the circuit board are the transmission and reception control unit 334 and the receiver unit 335. The connecting section 210 includes an integrated circuit apparatus 500. The integrated circuit apparatus 500 includes a transmission unit 332.

In a case where ultrasonic waves are transmitted, the transmission and reception control unit 334 issues a transmission command to the transmission unit 332, and the transmission unit 332 receives the transmission command, amplifies the drive signal to a high voltage, and outputs a drive voltage. The receiver unit 335 includes a limiter circuit (not shown), and the limiter circuit cuts off the drive voltage. In a case where reflected waves of the ultrasonic waves are received, the receiver unit 335 receives a signal of the reflected waves detected by the ultrasonic transducer device 200. The receiver unit 335 processes (for example, amplification processing, A/D conversion processing, or the like) the signal of the reflected waves on the basis of a reception command coming from the transmission and reception control unit 334, and transmits the processed signal to the processing unit 420. The processing unit 420 generates display image data on the basis of the signal, and causes the display unit 440 to produce a display.

The ultrasonic measurement apparatus of the present embodiment is not limited to being a medical ultrasonic diagnostic apparatus such as described above, but rather can be applied to a variety of electronic machines. For example, conceivable instances of electronic machines to which the ultrasonic transducer device has been applied include a diagnostic machine for nondestructively inspecting the interior of a building or the like, or a user interface machine for detecting movement of a user's finger by the reflection of ultrasonic waves.

Figure 10A:
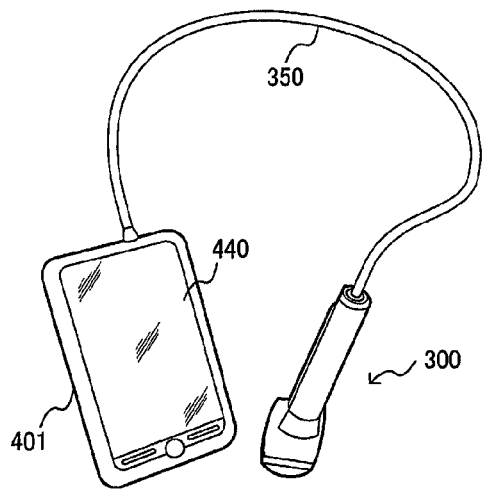
FIG. 10A is an example of a specific configuration for an ultrasonic diagnostic apparatus.
Figure 10B:
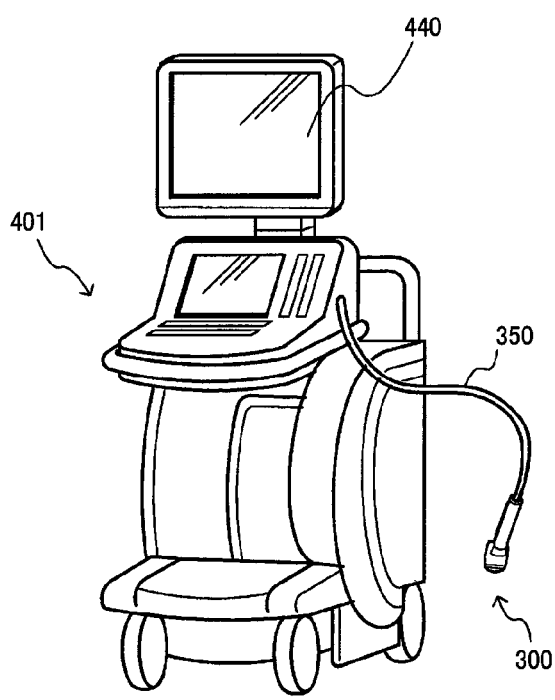
FIG. 10B is the example of the specific configuration for the ultrasonic diagnostic apparatus.

FIGS. 10A and 10B illustrate examples of a specific configuration for the ultrasonic diagnostic apparatus 400 of the present embodiment. FIG. 10A illustrates a portable ultrasonic diagnostic apparatus 400, and FIG. 10B illustrates a floor-standing ultrasonic diagnostic apparatus 400.

Both the portable version and the floor-standing version of the ultrasonic diagnostic apparatus 400 include the ultrasonic probe 300, a cable 350, and the ultrasonic diagnostic apparatus main body 401. The ultrasonic probe 300 is connected to the ultrasonic diagnostic apparatus main body 401 by the cable 350. The ultrasonic diagnostic apparatus main body 401 includes the display unit 440 for displaying the display image data.

Figure 10C:
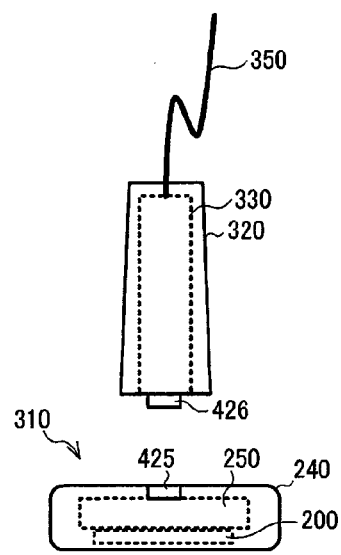
FIG. 10C is an example of a specific configuration for an ultrasonic probe.

FIG. 10C illustrates a specific configuration example for the ultrasonic probe 300 of the present embodiment. The ultrasonic probe 300 includes the probe head 310 and a probe main body 320, and, as illustrated in FIG. 10C, the probe head 310 can be attached or detached to/from the probe main body 320.

The probe head 310 includes the ultrasonic transducer device 200, the probe base 250, the probe housing 240, and a probe head-side connector 425.

The probe main body 320 includes the processing apparatus 330 and a probe main body-side connector 426. The probe main body-side connector 426 is connected to the probe head-side connector 425. The probe main body 320 is connected to the ultrasonic diagnostic apparatus main body 401 by the cable 350.

Though the present embodiment has been described in greater detail above, it shall be readily understood by a person skilled in the art that there are numerous possible modifications which do not substantially depart from the novel features and effects of the present invention. As such, the modification examples of such description are understood to all also be included in the scope of the present invention. For example, a phrase mentioned at least once in the specification or accompanying drawings together with a different phrase of broader or similar meaning can also be replaced with the different phrase in any portion in the specification or accompanying drawings. Also, the configurations and operations of the ultrasonic transducer device, the probe head, the ultrasonic probe, the electronic machine, and the ultrasonic diagnostic apparatus are also not limited to being what is described in the present embodiment, but rather a variety of modifications can be implemented.

The entire disclosure of Japanese Patent Application No. 2012-226671, filed Oct. 12, 2012 is expressly incorporated by reference herein.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer device comprising:
a substrate having a first surface and a second surface which opposes the first surface;
ultrasonic transducer elements disposed on the first surface of the substrate and arranged in a sheet shape in a predetermined arraying; and
a sheet-shaped member disposed on the second surface of the substrate,
the substrate including wall sections that partition the ultrasonic transducer elements neighboring each other, the substrate being disposed between the ultrasonic transducer elements and the sheet-shaped member, the wall sections and the sheet-shaped member being bonded together, and the sheet-shaped member including a plurality of first groove sections formed so as to correspond to each of the ultrasonic transducer elements.

2. The ultrasonic transducer device according to claim 1, wherein the sheet-shaped member further includes a second groove section for bundling together the first groove sections.

3. The ultrasonic transducer device according to claim 2, wherein the sheet-shaped member includes a through hole connecting the second groove section and an exterior.

4. The ultrasonic transducer device according to claim 2, wherein the sheet-shaped member includes a third groove section that is connected with an exterior but is not connected with the first groove sections nor with the second groove section, at a position opposing a surrounding region of a region of the substrate where the wall sections are provided.

5. The ultrasonic transducer device according to claim 2, wherein the first groove sections are provided along a first direction, the second groove section is provided along a second direction different from the first direction, at a position opposing a surrounding region of a region of the substrate where the wall sections are provided, and one ends of the first groove sections are joined to the second groove section.

6. The ultrasonic transducer device according to claim 5, wherein the sheet-shaped member includes a third groove section which is connected with an exterior but is not connected with the first groove sections nor with the second groove section, at the position opposing the surrounding region, the third groove section either is provided along the first direction on a region that runs along a first edge of the sheet-shaped member in the first direction or a second edge opposite to the first edge in the first direction, or is provided along the second direction on a region that runs along a third edge of the sheet-shaped member in the second direction or a fourth edge an opposite to the third edge, and a first end of the third groove section is separated from both the first groove sections and the second groove section and a second end of the third groove section is bonded to one of the first to fourth edges of the sheet-shaped member.

7. The ultrasonic transducer device according to claim 1, wherein each of the ultrasonic transducer elements includes a vibrating membrane blocking off between the wall sections, and a piezoelectric element section provided on the vibrating membrane, the piezoelectric element section including a lower electrode provided on the vibrating membrane, a piezoelectric body membrane at least partially covering the lower electrode, and an upper electrode at least partially covering the piezoelectric body membrane.

8. A probe head, provided with the ultrasonic transducer device according to claim 1.

9. An ultrasonic probe comprising:

the probe head according to claim 8; and a processing apparatus configured to process a signal coming from the ultrasonic transducer device.

10. An electronic machine, provided with the ultrasonic probe according to claim 9.

11. An ultrasonic diagnostic apparatus comprising:

the ultrasonic probe according to claim 9; and a display unit configured to display image data for display.

12. The ultrasonic transducer device according to claim 1, wherein a thickness of each wall section is smaller than a height of each wall section.

13. An ultrasonic transducer device comprising:

a substrate having a first surface and a second surface which opposes the first surface;

an ultrasonic transducer element disposed on the first surface of the substrate; and a sheet-shaped member disposed on the second surface of the substrate, the substrate including an opening that is separated by a wall section, the substrate being disposed between the ultrasonic transducer element and the sheet-shaped member, the wall section and the sheet-shaped member being bonded together, and the sheet-shaped member including a first groove section formed to correspond to the ultrasonic transducer element.

14. The ultrasonic transducer device according to claim 13, wherein a thickness of the wall section is smaller than a height of the wall section.

* * * * *